(12) United States Patent
Thal

(10) Patent No.: US 8,419,769 B2
(45) Date of Patent: Apr. 16, 2013

(54) ADJUSTABLE LOOP KNOTLESS ANCHOR

(76) Inventor: Raymond Thal, McLean, VA (US)

( * ) Notice: Subject to any disclaimer, the term of this patent is extended or adjusted under 35 U.S.C. 154(b) by 681 days.

(21) Appl. No.: 12/289,982

(22) Filed: Nov. 7, 2008

(65) Prior Publication Data

US 2009/0138042 A1  May 28, 2009

Related U.S. Application Data

(60) Provisional application No. 60/996,225, filed on Nov. 7, 2007.

(51) Int. Cl.
*A61B 17/04* (2006.01)
(52) U.S. Cl.
USPC .......................................... 606/232
(58) Field of Classification Search ............ 606/148, 606/151, 157, 232, 300–321
See application file for complete search history.

(56) References Cited

U.S. PATENT DOCUMENTS

| | | | | |
|---|---|---|---|---|
| 5,584,835 A * | 12/1996 | Greenfield | ..................... | 606/232 |
| 6,045,574 A * | 4/2000 | Thal | .............................. | 606/232 |
| 6,972,027 B2 * | 12/2005 | Fallin et al. | .................... | 606/232 |
| 6,991,636 B2 * | 1/2006 | Rose | .............................. | 606/148 |
| 2001/0008971 A1 * | 7/2001 | Schwartz et al. | ............. | 606/232 |
| 2002/0019649 A1 * | 2/2002 | Sikora et al. | .................. | 606/232 |
| 2004/0147958 A1 * | 7/2004 | Lam et al. | ..................... | 606/232 |
| 2006/0106423 A1 * | 5/2006 | Weisel et al. | ................. | 606/232 |

* cited by examiner

*Primary Examiner* — Corrine M McDermott
*Assistant Examiner* — Alexander Orkin
(74) *Attorney, Agent, or Firm* — Welsh Flaxman & Gitler LLC

(57) ABSTRACT

An adjustable loop knotless anchor assembly having an adjustable loop suture element that utilizes an adjustable or sliding knot for length adjustment during a tissue repair. The slidable knot is located on a sleeve that is placed into a bone mass for capturing an anchor element. The anchor element captures the adjustable loop and then is inserted into the sleeve. The anchor element is adjusted for securing it in a locked position within the sleeve for secure attachment of the anchor element therein.

7 Claims, 3 Drawing Sheets

ADJUSTABLE LOOP KNOTLESS ANCHOR

CROSS REFERENCE TO RELATED APPLICATIONS

This application is based on U.S. Provisional Patent Application Ser. No. 60/996,225, filed Nov. 7, 2007.

BACKGROUND OF THE INVENTION

The application claims benefit of U.S. Provisional Patent Application Ser. No. 60/996,225 filed Nov. 7, 2007.

Soft tissues, such as tendons and ligaments, generally are attached to bone by small collageaous fibers. These connections are strong but permit the tendons and ligaments to be flexible. When a tissue, or a portion of a tissue, is torn away from the bone and requires repair, a surgeon is often required to repair the detached soft tissue with sutures, which are passed through bone tunnels and tied. A number of devices have been developed for securing a ligament or tendon to a bone mass. These devices can be used in place of bone tunneling techniques. These attachment devices are usually anchor element through extensive surgical incisions and, in some circumstances, by arthroscopic surgical techniques. The pulse of bone tunnels for repair can be difficult and generally require large open incisions. Recently, through the advent of endoscopic surgery, where the surgeon looks into a joint cavity with a telescope, there has been a trend to repair soft tissues back to bone through small incisions called portals. The unique free loop knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as prostheses, to bone. A suture anchor assembly is a device, which utilizes small anchors with suture materials attached thereto. A device, such as a screw, is anchor into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during endoscopic surgery and sometimes even in conventional open surgery.

Knotless anchor assemblies have been popular and are embodied in a number of prior patents such as U.S. Pat. No. 6,045,574 wherein there is provided an assembly with an anchor means having a snag means, and a hollow sleeve element with a loop suture element attached thereto, wherein the snag means captures a loop suture element of the hollow sleeve element to draw tissue into secure attachment with a bone mass.

A difficulty with the existing structures is the ability to modify or adjust the length of the suture element that draws the tissue to the bone for secure attachment.

To overcome this and other deficiencies in the existing structures, the present invention provides a suture element in conjunction with the structure that is adjustable.

To overcome additional deficiencies in the existing structures, it is an objective of the present invention to provide a sleeve that enables the anchor element to be locked in place.

SUMMARY OF THE INVENTION

An adjustable loop knotless anchor assembly having an adjustable loop suture element that utilizes an adjustable or sliding knot for length adjustment during a tissue repair. The slidable knot is located on a suture loop that is captured in a cylindrical hollow or U-shaped sleeve that is placed into a bone mass for capturing an anchor element. The anchor element captures the adjustable loop and then is inserted and locked into or onto the sleeve. The anchor element is adjusted for securing it in a locked position within the sleeve or below a hollow sleeve for secure attachment of the anchor element therewith.

DETAILED DESCRIPTION OF THE INVENTION

Figure 1:
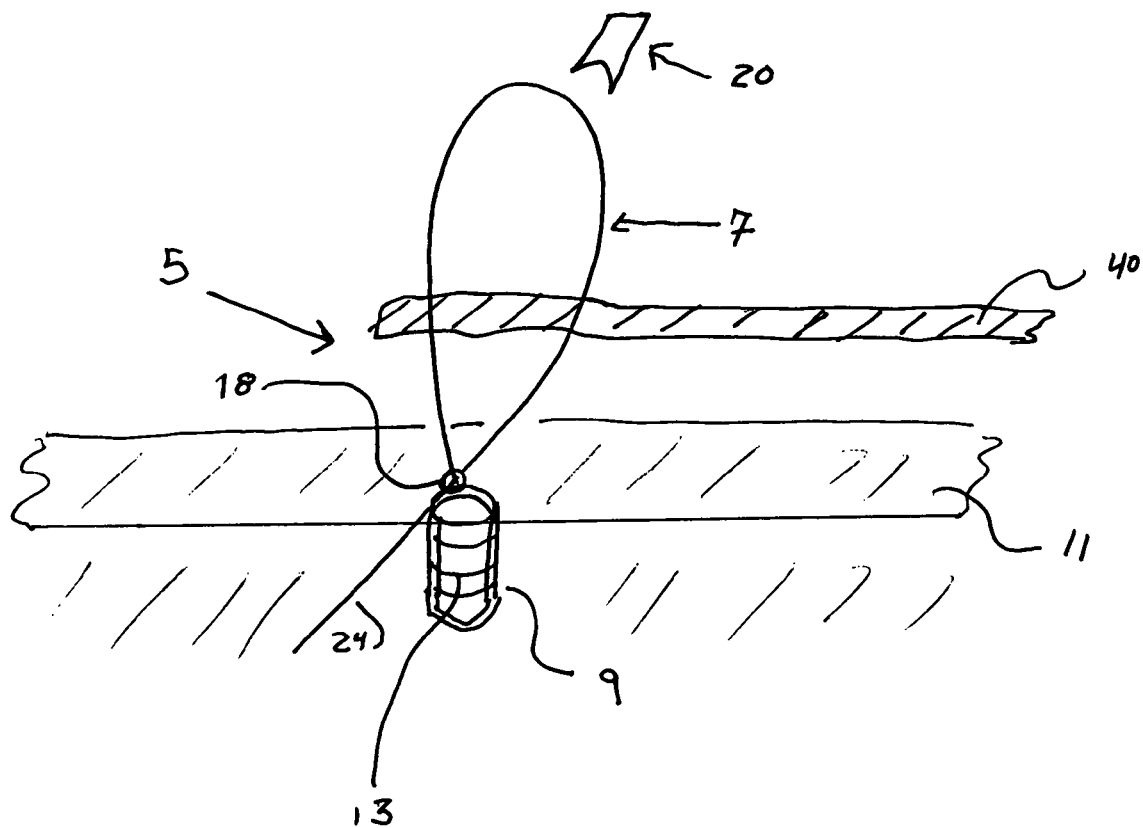
FIG. 1 discloses a side view of the assembly anchor element into a bone mass.
Figure 2:
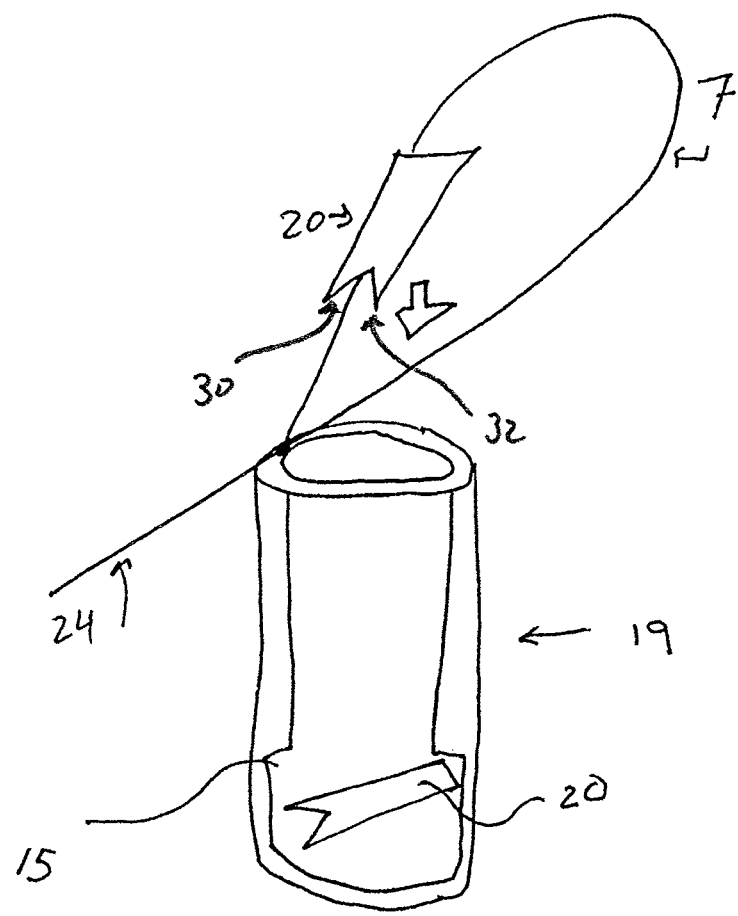
FIG. 2 depicts a close up view of the anchor element capturing the adjustable suture loop element and the anchor element locked into the sleeve.
Figure 3:
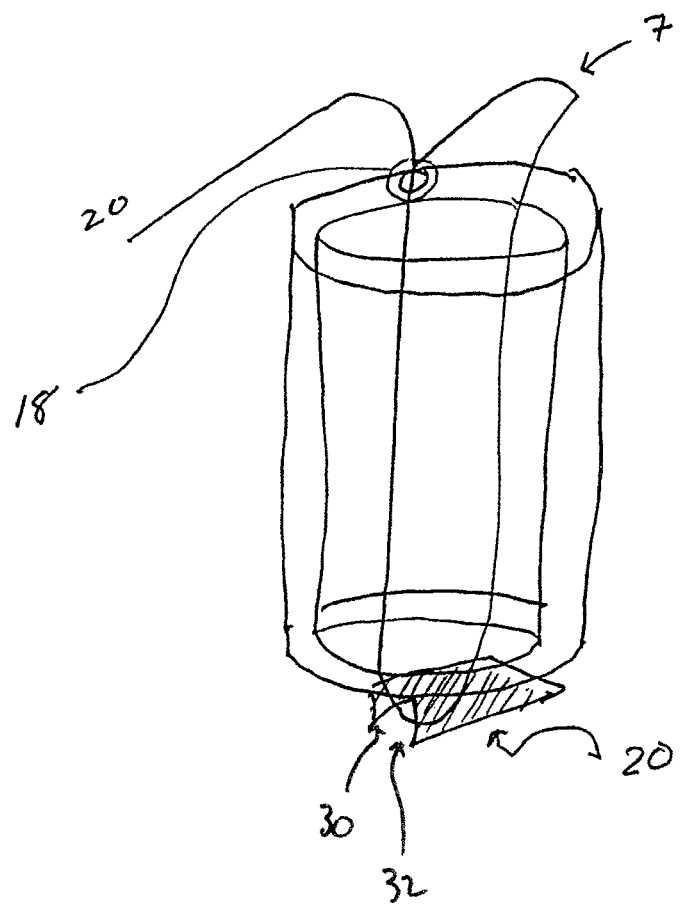
FIG. 3 depicts an alternate hollow cylindrical sleeve with an anchor element locked below.

The adjustable loop knotless suture anchor assembly 5 is composed of an adjustable suture loop element 7 that is attached to a sleeve 9 via an anchor element 20 and can be inserted into a bone mass 11. This is displayed in FIG. 1. A hollow or U-shaped sleeve 9 is secured to a bone mass 11 by any suitable method. External threads 13 on the sleeve are preferable for attachment to bone. The inside of the sleeve 9 can have a locking means 15 therein for holding the anchor element 20 in place. The profile of the locking means 15 has a shape meeting with the anchor element to securely lock the anchor element 20 within the sleeve 9. The locking of the anchor element 20 to the sleeve 9 is seen in FIG. 2, which shows the anchor element 20 locked within the sleeve 9. Alternatively, the anchor element 20 can be inserted into a hollow sleeve 9 and can lock or be captured by the bottom of the hollow sleeve 9 after insertion. This is depicted in FIG. 3.

At least one adjustable suture loop element 7 is captured by the snag means of the anchor element 20 and suture loop inserted into the sleeve 9. The adjustable suture loop element 7 can be a separate non-attached suture loop or can be attached to the sleeve 9. The suture loop 7 includes a one-way sliding knot 18, and the knot can be captured either within the sleeve 9 or can be located elsewhere on the loop 7 once the loop is inserted into the sleeve. The one-way sliding knot 18 allows the size of the suture loop element 7 to be adjusted in length by pulling on a strand of suture 24 attached to the sliding knot 18 and the adjustable loop 7. After the anchor element 20 is secured within the sleeve 9, the loop 7, capturing the tissue 40, is adjusted to the proper size to securely retain the tissue to a bone mass. When the loop 7 is shortened by pulling the suture strand 24, the tissue 40 is drawn into engagement with the bone mass 11 for facilitating healing and a repair. The knot 18 is a one-way slip knot that allows movement in only one direction and the tension created in the loop causes the knot to tighten and maintain the loop in a fixed size for the repair. Such adjustment facilitates various size repairs and also enables the doctor to select a desired tension.

The anchor element 20 has a catch means 30 at a suitable location, such as a leading edge 32, to capture the loop 7. Once the loop 7 is captured, the anchor element 20 is pushed into the sleeve and is locked within the sleeve 9, allowing the loop to capture tissue and pull same against the bone for a repair. The anchor element 20 may lock within the sleeve by any suitable method including compression, rotation, expansion, friction, twist, flip and catch, or arcs.

FIG. 2 shows one manner in which the anchor element 20 rotates and catches within the sleeve 9 for a secure connection between the anchor element 20 and sleeve 9. The repair tension is adjusted by adjusting the loop length without any ratcheting between the sleeve and anchor element being necessary.

FIG. 3 shows an alternative method where the anchor element 20 is inserted into a hollow sleeve 9 and catches or locks on the bottom of the sleeve 9. Once the anchor element 20 is locked, the adjustable suture loop element 7 is shortened by pulling on the suture strand 24 to a desired length for holding a tissue into contact with a bone mass for a repair.

If desired, one can use more than one adjustable suture loop element to facilitate the repair in one sleeve or one can use multiple sleeves with one or more adjustable suture loop elements.

What is claimed is:

1. An adjustable loop knotless anchor assembly comprising:
   an anchor element with a snag means located on an end;
   a hollow cylindrical or cup-shaped sleeve having a first end and a second end; and
   at least one adjustable suture loop element directly attached to the first end of the sleeve, the at least one adjustable suture loop element having a one-way slidable knot along its length for adjusting the length of the at least one suture loop element, wherein the snag means captures said at least one loop suture loop element during or prior to insertion of the anchor element into the sleeve and locks the anchor element into the sleeve and the length of the at least one suture loop element is then adjusted via the one-way slidable knot to draw a tissue into secure attachment with a bone mass wherein the one-way slidable knot is located at a point where the at least one suture loop element is attached to the first end of the sleeve.

2. The adjustable loop knotless assembly of claim 1, further comprising a locking means within the sleeve to facilitate capture of the anchor element in the sleeve.

3. The adjustable loop knotless assembly of claim 1, wherein the snag means is a recess in the leading edge of the anchor element.

4. The adjustable loop knotless assembly of claim 1, further comprising threads on an exterior of said sleeve to facilitate secure attachment of said sleeve to the bone mass.

5. The adjustable loop knotless assembly of claim 1, wherein the anchor element with the snag means is secured with the adjustable suture loop element within the sleeve.

6. The adjustable loop knotless assembly of claim 1, wherein the anchor element with the snag means is locked with the adjustable suture loop element on a bottom of the sleeve.

7. The adjustable loop knotless assembly of claim 1, wherein the one-way slidable knot is positioned at a point of direct attachment of the adjustable suture loop element of the sleeve.

* * * * *